(12) United States Patent
DeJovin

(10) Patent No.: US 8,394,800 B2
(45) Date of Patent: *Mar. 12, 2013

(54) METHOD FOR TREATING PSORIASIS

(75) Inventor: Jack A. DeJovin, New Brunswick, NJ (US)

(73) Assignee: Galderma Laboratories, L.P., Fort Worth, TX (US)

( * ) Notice: Subject to any disclaimer, the term of this patent is extended or adjusted under 35 U.S.C. 154(b) by 183 days.

This patent is subject to a terminal disclaimer.

(21) Appl. No.: 12/621,942

(22) Filed: Nov. 19, 2009

(65) Prior Publication Data

US 2011/0118267 A1 May 19, 2011

(51) Int. Cl.
*A61K 31/495* (2006.01)
*A01N 43/50* (2006.01)
*A01N 33/02* (2006.01)

(52) U.S. Cl. ............... 514/249; 514/401; 514/649

(58) Field of Classification Search ............... None
See application file for complete search history.

(56) References Cited

U.S. PATENT DOCUMENTS

| | | |
|---|---|---|
| 3,278,447 A | 10/1966 | McNicholas |
| 3,560,501 A | 2/1971 | Walker |
| 3,594,380 A | 7/1971 | Sulkowski |
| 3,723,432 A | 3/1973 | Ott |
| 3,736,297 A | 5/1973 | Bracke |
| 3,740,442 A | 6/1973 | Ott |
| 3,890,319 A | 6/1975 | Danielewicz et al. |
| 4,029,792 A | 6/1977 | Danielewicz et al. |
| 4,164,570 A | 8/1979 | Clough et al. |
| 4,201,211 A | 5/1980 | Chandrasekaran et al. |
| 4,256,763 A | 3/1981 | McHugh |
| 4,285,967 A | 8/1981 | Gubernick et al. |
| 5,021,416 A | 6/1991 | Gluchowski |
| 5,077,292 A | 12/1991 | Gluchowski |
| 5,112,822 A | 5/1992 | Gluchowski |
| 5,130,441 A | 7/1992 | Gluchowski |
| 5,198,442 A | 3/1993 | Gluchowski |
| 5,204,347 A | 4/1993 | Gluchowski |
| 5,237,072 A | 8/1993 | Gluchowski |
| 5,300,504 A | 4/1994 | Gluchowski |
| 5,326,763 A | 7/1994 | Gluchowski et al. |
| 5,373,010 A | 12/1994 | Gluchowski et al. |
| 5,418,234 A | 5/1995 | Gluchowski et al. |
| 5,424,078 A | 6/1995 | Dziabo et al. |
| 5,442,053 A | 8/1995 | della Valle et al. |
| 5,552,403 A | 9/1996 | Burke et al. |
| 5,561,132 A | 10/1996 | Burke et al. |
| 5,587,376 A | 12/1996 | Burke et al. |
| 5,693,646 A | 12/1997 | Jones et al. |
| 5,696,127 A | 12/1997 | Jones et al. |
| 5,703,077 A | 12/1997 | Burke et al. |
| 5,714,486 A | 2/1998 | Burke et al. |
| 5,720,962 A | 2/1998 | Ivy et al. |
| 5,721,237 A | 2/1998 | Myers et al. |
| 5,736,165 A | 4/1998 | Ripley et al. |
| 5,753,637 A | 5/1998 | Fried |
| 5,756,503 A | 5/1998 | Burke et al. |
| 5,773,440 A | 6/1998 | Burke et al. |
| 5,916,574 A | 6/1999 | Fried et al. |
| 6,117,871 A | 9/2000 | Maurer et al. |
| 6,117,877 A | 9/2000 | Fogel |
| 6,194,415 B1 | 2/2001 | Wheeler et al. |
| 6,248,741 B1 | 6/2001 | Wheeler et al. |
| 6,284,765 B1 | 9/2001 | Caffrey |
| 6,294,553 B1 | 9/2001 | Gil et al. |
| 6,323,204 B1 | 11/2001 | Burke et al. |
| 6,387,383 B1 | 5/2002 | Dow et al. |
| 6,432,934 B1 | 8/2002 | Gilbard |
| 6,441,047 B2 | 8/2002 | DeSantis, Jr. |
| 6,444,681 B1 | 9/2002 | Flavahan et al. |
| 6,465,464 B2 | 10/2002 | Wheeler et al. |
| 6,468,989 B1 | 10/2002 | Chang et al. |
| 6,517,847 B2 | 2/2003 | Dow et al. |
| 6,534,048 B1 | 3/2003 | Borgman |
| 7,014,858 B2 | 3/2006 | Ashley |
| 7,439,241 B2 | 10/2008 | DeJovin et al. |
| 7,838,563 B2 | 11/2010 | DeJovin et al. |
| 2002/0197300 A1 | 12/2002 | Schultz et al. |
| 2003/0017199 A1 | 1/2003 | Woodward et al. |
| 2003/0068343 A1 | 4/2003 | Muizzuddin et al. |
| 2003/0077301 A1 | 4/2003 | Maibach et al. |
| 2003/0087962 A1 | 5/2003 | Demopulos et al. |
| 2003/0229088 A1 | 12/2003 | Gil et al. |
| 2004/0092482 A1 | 5/2004 | Gupta |
| 2004/0156873 A1 | 8/2004 | Gupta |
| 2004/0220259 A1 | 11/2004 | Yu et al. |
| 2004/0242588 A1 | 12/2004 | DeJovin et al. |
| 2004/0254252 A1 | 12/2004 | Engles et al. |
| 2004/0266776 A1 | 12/2004 | Gil et al. |
| 2005/0020600 A1 | 1/2005 | Scherer |
| 2005/0059664 A1 | 3/2005 | Gil et al. |
| 2005/0059744 A1 | 3/2005 | Donello et al. |
| 2005/0124593 A1* | 6/2005 | Bernstein ............ 514/171 |
| 2005/0165079 A1 | 7/2005 | Shanler et al. |
| 2005/0276830 A1 | 12/2005 | DeJovin et al. |
| 2006/0264515 A1 | 11/2006 | Dejovin et al. |
| 2007/0082070 A1 | 4/2007 | Stookey et al. |
| 2007/0207222 A1 | 9/2007 | Yu et al. |
| 2008/0044497 A1* | 2/2008 | Sussan et al. ............ 424/725 |
| 2009/0061020 A1* | 3/2009 | Theobald et al. ......... 424/617 |
| 2010/0021402 A1 | 1/2010 | DeJovin et al. |

FOREIGN PATENT DOCUMENTS

| | | |
|---|---|---|
| EP | 1090630 A1 | 4/2001 |
| EP | 2090307 A1 | 8/2009 |
| GB | 1381979 A | 1/1975 |
| WO | 9100088 A1 | 1/1991 |
| WO | 9613267 A2 | 5/1996 |
| WO | 9625163 A1 | 8/1996 |
| WO | 9836730 A2 | 8/1998 |
| WO | 0076502 A1 | 12/2000 |
| WO | 2004105703 A2 | 12/2004 |
| WO | 2005002580 A1 | 1/2005 |
| WO | 2005010025 A2 | 2/2005 |

OTHER PUBLICATIONS

Schön et al. (N England J Med. 352:1899-912, 2005).*

(Continued)

*Primary Examiner* — Bong-Sook Baek
(74) *Attorney, Agent, or Firm* — Panitch Schwarze Belisario & Nadel LLP

(57) ABSTRACT

Methods and kits for treating or preventing psoriasis or a symptom associated with psoriasis in a subject are described. The methods involve topical applications to the subject a therapeutically effective amount of an α2 adrenergic receptor agonist, such as brimonidine.

10 Claims, No Drawings

OTHER PUBLICATIONS

Int'l Search Report issued on Mar. 29, 2011 in Int'l Application No. PCT/US2010/057184; Written Opinion.
Arndt et al, "Manual of Dermatologic Therapeutics", 7th Ed., pp. 176-177 (2007).
Berge et al, "Pharmaceutical Salts", Journal of Pharmaceutical Sciences, vol. 66, No. 1, pp. 1-19 (1977).
Bockman et al, "Binding and Functional Characterization of Alpha-2 Andrenergic Receptor Subtypes on Pig Vascular Endothelium", J. Pharmacol. Exp. Therapeutics, vol. 267, pp. 1126-1133 (1993).
Burke et al, "Preclinical Evaluation of Brimonidine", Survey of Ophthalmology, vol. 41, pp. S9-S18 (1996).
Chein et al, "Corneal and conjunctival/scleral penetration of p-aminoclonidine, AGN 190342 and clonidine in rabbit eyes", Current Eye Research, vol. 9, No. 11 pp. 1051-1059 (1990).
Chotani et al, "Silent asc-adrenergic receptors enable cold-induced vasoconstriction in cutaneous arteries", Am. J. Physiol. Heart Circ. Physiol., vol. 278, pp. H1075-H1083 (2000).
Cunliffe et al, Br. Med. J. 105 (1977).
Freedman et al, "Estrogen raises the sweating threshold in postmenopausal women with hot flashes", Fertility and Sterility, vol. 77, No. 3, pp. 487-490 (2002).
Fuchs et al, "Heat, but not Mechanical Hyperalgesia, following Andrenergic Injections in Normal Human Skin", Pain, Vol. 90, Nos. 1-2, pp. 15-23 (2001).
Gennaro, "Remington: The Science and Practice of Pharmacy", 19th Ed., pp. 866-885, 1517-1518, 1577-1597, 1672-1673 (1995).
Guarrera et al, "Flushing in Rosacea: A Possible Mechanism", Arch. Dermatol. Res., vol. 272, pp. 311-316 (1982).
Jeyara et al, "Cooling Evokes Redistribution of a2C-Andrenoceptors from Golgi to Plasma Membrane in Transfected Human Embryonic Kidney 293 Cells", Molecular Pharmacology, vol. 60, No. 6, pp. 1195-1200 (2001).
Lindgren et al, "Effects of Some Antihypertensive Drugs on Cutaneous Blood Flow and Inflammatory Skin Responses Following Allergen Challenge in Guinea Pigs", Pharmacology and Toxicology, vol. 60, pp. 364-367 (1987).
Material Safety Data Sheet, pp. 1-2 (1997).
McGhie, "Brimonidine: An alpha-2 adrenergic agonist for glaucoma", Journal of the Pharmacy Society of Wisconsin, May/Jun. 2001, pp. 32-36.
Morrison et al, "Andrenergic Modulation of a Spinal Sympathetic Reflex in the Rat", J. Pharmacol. Experim. Therap., vol. 273, No. 1, pp. 380-385 (1995).
Nakamura et al, "Peripheral analgesic action of clonidine: mediation by release of endogenous enkephlin-like substances", European Journal of Pharmacology, vol. 146, pp. 223-228 (1988).
Nielsen et al, "Postjunctional a2-adrenoceptors mediate vasoconstriction in human subcutaneous resistance vessels", Br. J. Pharmacol., vol. 97, pp. 829-834 (1989).
Ramey et al, "Rhinitis Medicamentosa", J Investig Allergol Clin Immunol, vol. 16, No. 3, pp. 148-155 (2006).
Rebora, "The Management of Rosacea", Am. J. Clin. Dermatol., vol. 3, No. 7, pp. 489-496 (2002).
Sakakibara et al, "Treatment of Primary Erythromelalgia with Cyproheptadine", Journal of the Autonomic Nervous System, vol. 58, Nos. 1-2, pp. 121-122 (1996).
Scruggs, "The Teardrop Sign: a Rare Dermatological Reaction to Brimonidine", Br. J. Opthalmol., vol. 84, pp. 671-672 (2000).
Shanler et al, "Arch Dermatol", vol. 143, No. 11, pp. 1369-1371 (2007).
Waldron et al, "Relative Contribution of Different Vascular Beds to the Pressor Effects of a-Adrenoceptor Agonists and Vasopressin in Pithed Rats: Radioactive Microsphere Determination", J. Auton. Pharmac., vol. 5, pp. 333-338 (1985).
Walters, "Development and Use of Brimonidine in Treating Acute and Chronic Elevations of Intraocular Pressure: A Review of Safety, Efficacy, Dose Response, and Dosing Studies", Survey of Ophthalmology, vol. 41, pp. S19-S26 (1996).
Webster, "Rosacea and related disorders", Dermatology, vol. 1, Chapter 39, pp. 545-552 (2003).
Wilkin et al, J. Am. Acad. Dermatol., vol. 46, pp. 584-587 (2002).
Wilkin, "Effect of Subdepressor Clonidine on Flushing Reactions in Rosacea", Arch. Dermatol., vol. 119, pp. 211-214 (1983).
Wilkin, "Why is flushing limited to a mostly facial cutaneous distribution?", J. Am. Acad. Dermatol., vol. 19, pp. 309-313 (1988).
Wymenga et al, "Management of Hot Flushes in Breast Cancer Patients", Acta Ocologica, vol. 41, No. 3, pp. 269-275 (2002).
Yaksh et al, "Reversal of Nerve Ligation-Induced Allodynia by Spinal Alpha-2 Andrenoceptor Agonists", J. Pharmacol. Experim. Therap., vol. 272, No. 1, pp. 207-214 (1995).
Culp et al., "Rosacea: A Review," Pharmacy & Therapeutics, vol. 34, No. 1, pp. 38-45 (2009).
Roberson et al., "Psoriasis genetics: breaking the barrier," Trends in Genetics, vol. 26, No. 9, pp. 415-423 (2010).
Kurian et al., "Current Effective Topical Therapies in the Management of Psoriasis," Skin Therapy Letter, vol. 16, No. 1, pp. 4-7 (2011).
Korting et al., "Liposome encapsulation improves efficacy of betamethasone dipropionate in atopic eczema but not in psoriasis vulgaris," European Journal of Clinical Pharmacology, vol. 39, pp. 349-351 (1990).
Khandpur et al., "Topical immunomodulators in dermatology," Journal of Postgraduate Medicine, vol. 50, No. 2, pp. 131-139 (2004).
Ruffolo et al., "Receptor Interactions of Imidazolines: alpha-Adrenoceptors of Rat and Rabbit Aortae Differentiated by Relative Potencies, Affinities and Efficacies of Imidazoline Agonists," British Journal of Pharmacology, vol. 77, pp. 169-176 (1982).
Waugh et al., "Phe-308 and Phe-312 in Transmembrane Domain 7 Are Major Sites of alpha1-Adrenergic Receptor Antagonist Binding," The Journal of Biological Chemistry, vol. 276, No. 27, pp. 25366-25371 (2001).
Pigini et al., "Structure-Activity Relationship at alpha-Adrenergic Receptors Within a Series of Imidazoline Analogues of Cirazoline," Bioorganic & Medicinal Chemistry, vol. 8, pp. 883-888 (2000).
Hieble et al., "Alpha- and Beta-Adrenoceptors: From the Gene to the Clininc. 1. Molecular Biology and Adrenoceptor Subclassification," Journal of Medicinal Chemistry, vol. 38, No. 18, pp. 3415-3444 (1995).
Szabo, "Imidazoline antihypertensive drugs: a critical review on their mechanism of action," Pharmacology & Therapeutics, vol. 93, pp. 1-35 (2002).
Balogh et al., "3D QSAR models for alpha2a-adrenoceptor agonists," Neurochemistry International, vol. 51, pp. 268-276 (2007).
Ruffolo et al., "Alpha- and Beta-Adrenoceptors: From the Gene to the Clinic. 2. Structure-Activity Relationships and Therapeutic Applications," Journal of Medicinal Chemistry, vol. 38, No. 19, pp. 3681-3716 (1995).
Day et al., "Use of pimecrolimus cream in disorders other than atopic dermatitis," Journal of Cutaneous Medicine and Surgery, vol. 12, No. 1, pp. 17-26 (2008) (abstract only).
Kosari et al., "Case report: Fluocinonide-induced perioral dermatitis in a patient with psoriasis," Dermatology Online Journal, vol. 15, No. 3 (2009).
Duncan, "Differential inhibition of cutaneous T-cell-mediated reactions and epidermal cell proliferation by cyclosporin A, FK-506, and rapamycin," Journal of Investigative Dermatology, vol. 102, No. 1, pp. 84-88 (1994).
Nichols et al., "Structure-Activity Relationships for alpha-Adrenoceptor Agonists and Antagonists," Alpha-Adrenoceptors: Molecular Biology, Biochemistry and Pharmacology, ed: Robert R. Ruffolo, Jr., pub: Karger, pp. 75-114 (1991).
Pérez-Rivera et al, "Increased Reactivity of Murine Mesenteric Veins to Adrenergy Agonists: Functional Evidence Supporting Increased alpha1-Adrenoceptor Reserve in Veins Compared with Arteries," Journal of Pharmacology and Experimental Therapeutics, vol. 308, No. 1, pp. 350-357 (2004).
Hirafuji et al, "Noradrenaline stimulates 5-hydroxytryptamine release from mouse ileal tissues via alpha(2)- adrenoceptors," European Journal of Pharmacology, vol. 432, No. 2-3, pp. 149-152 (Dec. 7, 2001) (Abstract only).
Prisant, "Transdermal clonidine skin reactions," Journal of Clinical Hypertension, vol. 4, No. 2, pp. 136-138 (Mar.-Apr. 2002) (Abstract only).

Lueg et al, "Transdermal clonidine as an adjunct to sustained-release diltiazem in the treatment of mild-to-moderate hypertension," Clinical Therapeutics, vol. 13, No. 4, pp. 471-481 (Jul.-Aug. 1991) (Abstract only).

Holdiness, "A review of contact dermatitis associated with transdermal therapeutic systems," Contact Dermatitis, vol. 20, No. 1, pp. 3-9 (Jan. 1989) (Abstract only).

Schmidt et al, "Transdermal clonidine compared with hydrochlorothiazide as monotheraphy in elderly hypertensive males," Journal of Clinical Pharmacology, vol. 29, No. 2, pp. 133-139 (Feb. 1989) (Abstract only).

* cited by examiner

METHOD FOR TREATING PSORIASIS

BACKGROUND OF THE INVENTION

Psoriasis is a common, chronic recurring condition characterized by the eruption of circumscribed, discrete and confluent, reddish, silvery-scaled maculopapules, which occur predominantly on the elbows, knees, scalp, and trunk. Skin rapidly grows and accumulates at psoriatic plaques, i.e., red scaly patches. Psoriasis varies in severity from minor localized patches to complete body coverage. The common forms of the disease include, for example, psoriasis vulgaris, guttate psoriasis, flexural psoriasis, erythrodermic psoriasis, generalized pustular psoriasis and localized pustular psoriasis. The cause of psoriasis is not known, but it is believed to be inherent. It may be aggravated by multiple factors, such as stress, withdrawal of systemic corticosteroid, excessive alcohol consumption, and smoking.

Psoriasis is difficult to treat. Currently available treatments for psoriasis are of limited effectiveness in many patients and, generally, can be used only for a limited duration. For example, topical treatment with coal tar, dithranol (anthralin), corticosteroids like desoximetasone (Topicort), fluocinonide, vitamin D analogues (for example, calcipotriol), retinoids, Argan oil, etc., often irritates normal skin, cannot be used for long periods, and may cause an aggressive recurrence of the condition when the treatment stops. Phototherapy, such as daily, short, non-burning exposure to sunlight or with ultraviolet B (UVB) (315-280 nm) helped to clear or improve psoriasis in some, but not all, patients. Photochemotherapy, i.e., the combined therapy of psoralen and ultraviolet A phototherapy (PUVA), has also been used to treat psoriasis. However, PUVA is associated with nausea, headache, fatigue, burning, itching. Long-term PUVA treatment is associated with squamous cell carcinoma. Psoriasis can also be treated by systemic treatment, e.g., by injection or oral administration of medications, such as methotrexate, cyclosporine and retinoids. However, these medications are known to have toxic side effects, thus cannot be used too frequently. Patients undergoing systemic treatment are required to have regular blood and liver function tests, and pregnancy must be avoided for the majority of these treatments. Most people experience a recurrence of psoriasis after systemic treatment is discontinued. Biologics, such as Amevive®, Enbrel®, Humira®, and Remicade® and Raptiva®, are relatively new therapies that focus on specific aspects of the immune function leading to psoriasis. However, the long-term impact of the biologics on immune function is unknown. Raptiva® was withdrawn by its maker from the US market in April, 2009. They are very expensive and only suitable for very few patients with severe psoriasis.

Agonists of the α2 adrenoceptors have been used therapeutically for a number of conditions including hypertension, congestive heart failure, angina pectoris, spasticity, glaucoma, diarrhea, and for the suppression of opiate withdrawal symptoms (J. P. Heible and R. R. Ruffolo Therapeutic Applications of Agents Interacting with α-Adrenoceptors, p. 180-206 in *Progress in Basic and Clinical Pharmacology* Vol. 8, P. Lomax and E. S. Vesell Ed., Karger, 1991). Adrenoreceptor agonists, such as clonidine, have been primarily used orally, though a patch formulation is known.

Published US Patent Application US20050276830 discloses α2 adrenergic receptor agonists and their use for treating or preventing inflammatory skin disorders.

There remains a need of novel effective and safe methods and compositions for treating or preventing psoriasis and related symptoms. Such methods and compositions are described in the present application.

BRIEF SUMMARY OF THE INVENTION

It is now discovered that an α2 adrenergic receptor agonist is effective in treating or preventing psoriasis with no or little side effects.

In one general aspect, embodiments of the present invention relate to a method of treating or preventing psoriasis or a symptom associated therewith in a subject. The method comprises topically administering to a skin area of the subject a topical composition comprising a therapeutically effective amount of an α2 adrenergic receptor agonist and a pharmaceutically acceptable carrier, wherein the skin area is, or is prone to be, affected by psoriasis or the symptom associated therewith.

In another general aspect, embodiments of the present invention relate to a kit for treating or preventing psoriasis or a symptom associated therewith. The kit comprises:

(1) a topically administrable composition comprising a therapeutically effective amount of an $\alpha_2$ adrenergic receptor agonist and a pharmaceutically acceptable carrier; and (2) instructions for topically administering the topically administrable composition to a skin area of a subject for treating or preventing psoriasis or the symptom associated therewith, wherein the skin area is, or is prone to be, affected by psoriasis or the symptom associated therewith.

In a preferred embodiment, the $\alpha_2$ adrenergic receptor agonist used in embodiments of the present invention is brimonidine.

Other aspects, features and advantages of the invention will be apparent from the following disclosure, including the detailed description of the invention and its preferred embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, "psoriasis or a symptom associated therewith" is intended to encompass any type or classification of psoriasis and any symptom associated therewith. For example, the term "psoriasis or a symptom associated therewith" includes plaque psoriasis, pustular psoriasis, guttate psoriasis (small, drop like spots) and flexural psoriasis, nail psoriasis, psoriatic arthritis and erythrodermic psoriasis, and their associated symptoms. The term also includes nonpustular psoriasis, such as psoriasis vulgaris (chronic stationary psoriasis, plaque-like psoriasis), psoriatic erythroderma (erythrodermic psoriasis); and pustular psoriasis, such as generalized pustular psoriasis (pustular psoriasis of von Zumbusch) (liquid-filled yellowish small blisters), pustulosis palmaris et plantaris (palmoplantar pustulosis (primarily affecting the palms and the soles), pustular psoriasis of the Barber type, pustular psoriasis of the extremities), annular pustular psoriasis, acrodermatitis continua and impetigo herpetiformis, and their associated symptoms. The term also encompasses drug-induced psoriasis, inverse psoriasis (in the folds like of the underarms, navel, and buttocks), napkin psoriasis, and seborrheic-like psoriasis, and their associated symptoms.

The degree or the severity of the psoriasis may vary. The degree of severity is generally based on the proportion of body surface area affected, disease activity (degree of plaque redness, thickness and scaling), response to previous therapies, and the impact of the disease on the person. The term "psoriasis or a symptom associated therewith" encompasses the mild (affecting less than 3% of the body area), moderate (affecting 3-10% of the body area) or severe (more than 10% of the body area) psoriasis and its symptoms.

Psoriasis typically looks like red or pink areas of thickened, raised, and dry skin. It classically affects areas over the elbows, knees, and scalp. Essentially any body area may be involved. It tends to be more common in areas of trauma, repeat rubbing, use, or abrasions. Psoriasis has many different appearances. It may be small flattened bumps, large thick plaques of raised skin, red patches, and pink mildly dry skin to big flakes of dry skin that flake off. Sometimes pulling of one of these small dry white flakes of skin causes a tiny blood spot on the skin. This is medically referred to as a special diagnostic sign in psoriasis called the Auspitz sign.

Genital lesions, especially on the head of the penis, are common. Psoriasis in moist areas like the navel or area between the buttocks (intergluteal folds) may look like flat red patches. These atypical appearances may be confused with other skin conditions like fungal infections, yeast infections, skin irritation, or bacterial Staph infections.

On the nails, it can look like very small pits (pinpoint depressions or white spots on the nail) or as larger yellowish-brown separations of the nail bed called "oil spots." Nail psoriasis may be confused with and incorrectly diagnosed as a fungal nail infection.

On the scalp, it may look like severe dandruff with dry flakes and red areas of skin.

In view of the present disclosure, a skin area affected by psoriasis or is prone to be affected by psoriasis can be identified using any diagnostic signs or means known in the art, and can be treated by methods according to embodiments of the present invention.

As used herein, an "$\alpha 2$ adrenergic receptor agonist" or "agonist of $\alpha 2$ adrenoceptor" means a compound that binds to and selectively stimulates alpha adrenergic receptor subclass $\alpha_2$. Such compounds can have powerful vasoconstricting effects when introduced into the body of mammals, particularly humans.

As used herein, the term "alkyl" means a saturated, monovalent, unbranched or branched hydrocarbon chain. Examples of alkyl groups include, but are not limited to, (C1-C3) alkyl groups, such as methyl, ethyl, propyl, isopropyl, and (C4-C8) alkyl groups, such as 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl 2,2-dimethyl-1-butyl, 3,3-dimethyl-1-butyl, 2-ethyl-1-butyl, butyl, isobutyl, sec-butyl, t-butyl, pentyl, isopentyl, neopentyl, hexyl, heptyl, octyl, and the like. An alkyl group can be unsubstituted or substituted with one or more suitable substituents.

As used herein, the term "alkoxy" means an oxygen ether radical of an alkyl. Examples of alkoxy include, but are not limited to, methoxy, ethoxy, n-propoxy, sec-butoxy, t-butoxy, n-hexyloxy and the like. An alkoxy group can be unsubstituted or substituted with one or more suitable substituents.

When a particular group is "substituted" (e.g., alkyl, alkoxy), that group can have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the term "halogen" means fluorine, chlorine, bromine, or iodine. Correspondingly, the term "halo" means fluoro, chloro, bromo, and iodo.

As used herein, the name of a compound is intended to encompass all possible existing isomeric forms (e.g., optical isomer, enantiomer, diastereomer, racemate or racemic mixture), esters, prodrugs, metabolite forms, or pharmaceutically acceptable salts, of the compound. For example, "brimonidine" can be the compound (5-bromo-quinoxalin-6-yl)-(4,5-dihydro-1H-imidazol-2-yl)-amine, and any pharmaceutically acceptable salt of the compound, such as brimonidine tartrate.

The phrase "pharmaceutically acceptable salt(s)", as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Certain compounds used in the present invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

As used herein, the term "hydrate" means a compound of interest, or a pharmaceutically acceptable salt thereof that further includes a stoichiometric or non-stoichiometric amount of water bound to it by non-covalent intermolecular forces.

The term "topically administrable composition," a "topical composition," or a "topical formulation," as used herein, means any formulation or composition which is pharmaceutically and/or cosmetically acceptable for topical delivery of the specified compounds according to embodiments of the invention. Exemplary forms of formulation that can be used for topical administration in embodiments of the present invention include, but are not limited to, sprays, mists, aerosols, solutions, lotions, gels, creams, ointments, pastes, unguents, emulsions, and suspensions. The choice of topically administrable composition will depend on several factors, including the nature of the symptoms to be treated or prevented, the physiochemical characteristics of the particular compound to be administered and of other excipients present, their stability in the formulation, available manufacturing equipment, and cost constraints.

As used herein, the term "composition" is intended to encompass a product comprising the specified ingredient in the specified amount, as well as any product which results, directly or indirectly, from combinations of the specified ingredient in the specified amount.

As used herein, "carbomer" is the USP designation for various polymeric acids that are dispersible but insoluble in water. When the acid dispersion is neutralized with a base a clear, stable gel is formed. Carbomer 934P is physiologically inert and is not a primary irritant or sensitizer. Other carbomers include 910, 940, 941, and 1342.

As used herein, the term "subject" means any animal, preferably a mammal, most preferably a human, to whom will be or has been administered compounds or topical formulations according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of, or has been the object of observation or experiment of, treatment or prevention of psoriasis and symptoms associated therewith.

As used herein, the term "instructions" when used in the context of a kit includes a publication, a recording, a diagram or any other medium of expression which can be used to communicate the usefulness of the kit for its designated use. The instructions can, for example, be affixed to or included within a container for the kit.

In one embodiment, "treatment" or "treating" refers to an amelioration, or reversal of a disease or disorder, or at least one discernible symptom thereof, for example, treating psoriasis by lessening the redness and/or scaly patches on the skin. In another embodiment, "treatment" or "treating" refers to an amelioration, or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both.

In certain embodiments, compounds of interest are administered as a preventative measure. As used herein, "prevention" or "preventing" refers to a reduction of the risk of acquiring a given disease or disorder. In a preferred mode of the embodiment, the specified compounds are administered as a preventative measure to a subject having a predisposition to psoriasis, an inherent disease, even though symptoms of psoriasis are absent or minimal.

As used herein, a "therapeutically effective amount of an α2 adrenergic receptor agonist" means the amount of the α2 adrenergic receptor agonist that elicits the biological or medicinal response in a tissue system, animal or human that is being sought by a researcher, veterinarian, medical doctor or other clinician, which includes alleviation of the symptoms of the disease or disorder being treated. In a preferred embodiment, the therapeutically effective amount of an α2 adrenergic receptor agonist is effective to treat, improve the treatment of, or prophylactically prevent psoriasis or a symptom associated therewith.

In one general aspect, the present invention relates to a method of treating or preventing psoriasis or a symptom associated therewith in a subject. The method comprises topically administering to a skin area of the subject a composition comprising a therapeutically effective amount of an α2 adrenergic receptor agonist and a pharmaceutically acceptable carrier, wherein the skin area is, or is prone to be, affected by psoriasis or the symptom associated therewith under the treatment or prevention.

In an embodiment of the present invention, the α2 adrenergic receptor agonists include, but are not limited to, the α2 adrenergic receptor agonists disclosed in the published US Patent Application US20050276830, which is herein incorporated by reference in its entirety.

In one embodiment of the present invention, the α2 adrenergic receptor agonist is a compound of formula (I):

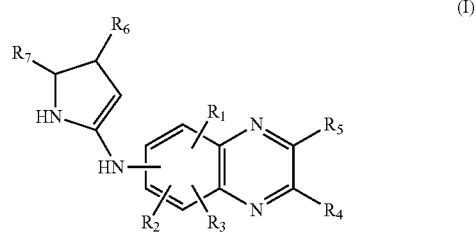

(I)

wherein each of $R_1$, $R_2$, and $R_3$ is independently hydrogen, halogen, alkyl, preferably unsubstituted alkyl, or alkoxy, preferably unsubstituted alkoxy; each of $R_4$ and $R_5$ is independently hydrogen, alkyl, preferably unsubstituted alkyl, or alkoxy, preferably unsubstituted alkoxy; and each of $R_6$ and $R_7$ is independently hydrogen, nitro, alkyl, preferably unsubstituted alkyl, or alkoxy, preferably unsubstituted alkoxy.

In a preferred embodiment, $R_6$ and $R_7$ are both hydrogen in formula (I).

In another preferred embodiment, $R_4$ and $R_5$ are both hydrogen in formula (I).

In one embodiment of the present invention, the α2 adrenergic receptor agonist is a compound of formula (Ia):

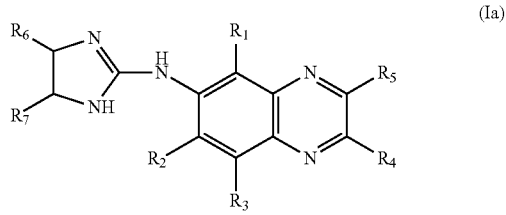

(Ia)

wherein each of $R_1$, $R_2$, and $R_3$ is independently hydrogen, hologen, alkyl, preferably unsubstituted alkyl, or alkoxy, preferably unsubstituted alkoxy; each of $R_4$ and $R_5$ is independently hydrogen, alkyl, preferably unsubstituted alkyl, or alkoxy, preferably unsubstituted alkoxy; and each of $R_6$ and $R_7$ is independently hydrogen, nitro, alkyl, preferably unsubstituted alkyl, or alkoxy, preferably unsubstituted alkoxy.

In a preferred embodiment, $R_6$ and $R_7$ are both hydrogen in formula (Ia).

In another preferred embodiment, $R_4$ and $R_5$ are both hydrogen in formula (Ia).

In still another preferred embodiment, $R_2$ and $R_3$ are both hydrogen and $R_1$ is halo, preferably, bromo, in formula (Ia).

In one embodiment of the present invention, the α2 adrenergic receptor agonist is a compound of formula (Ib):

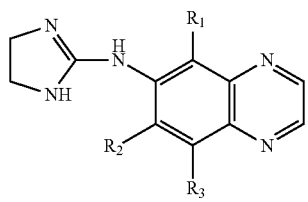
(Ib)

wherein each of $R_1$, $R_2$, and $R_3$ is independently hydrogen, halogen, alkyl, preferably, unsubstituted alkyl, or alkoxy, preferably, unsubstituted alkoxy.

In a preferred embodiment, $R_2$ and $R_3$ are both hydrogen and $R_1$ is halo, preferably, bromo, in formula (Ib)

In one embodiment of the present invention, the α2 adrenergic receptor agonist is a compound of formula (Ic):

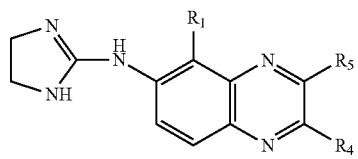
(Ic)

wherein $R_1$ is hydrogen, halogen, alkyl, preferably, unsubstituted alkyl, or alkoxy, preferably unsubstituted alkoxy.

In a preferred embodiment, $R_1$ is halo, more preferably, bromo; and each of $R_4$ and $R_5$ is independently hydrogen, alkyl, preferably, unsubstituted alkyl, or alkoxy, preferably, unsubstituted alkoxy, in formula (Ic).

In a preferred embodiment, at least one of $R_4$ and $R_5$ is hydrogen in formula (Ic).

In one embodiment of the present invention, the α2 adrenergic receptor agonist is a compound of formula (Id):

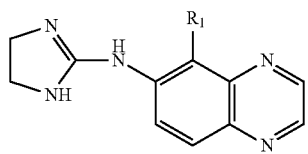
(Id)

wherein $R_1$ is hydrogen, halogen, alkyl, preferably, unsubstituted alkyl, or alkoxy, preferably, unsubstituted alkoxy.

In a preferred embodiment, $R_1$ is halo, more preferably, bromo, in formula (Id).

In another embodiment of the present invention, the α2 adrenergic receptor agonist is a compound of formula (II):

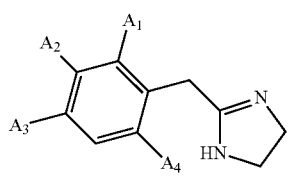
(II)

wherein each of $A_1$, $A_3$, and $A_4$ is independently hydrogen or alkyl; and $A_2$ is independently hydrogen or hydroxy.

In another embodiment of the present invention, the α2 adrenergic receptor agonist is a compound of formula (III):

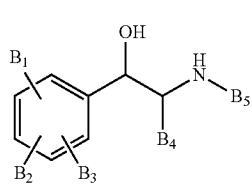
(III)

wherein each of $B_1$, $B_2$, and $B_3$ is independently hydrogen, hydroxy, or alkoxy, preferably methoxy; and each of $B_4$ and $B_5$ is independently hydrogen or alkyl.

Representative α2 adrenergic receptor agonists that can be used in the present invention include, but are not limited to, those listed in Table 1.

TABLE 1

| Representative α2 adrenergic receptor agonists | |
|---|---|
| Compound Formula | Compound Name |
| | (5-Bromo-quinoxalin-6-yl)-(4,5-dihydro-1H-imidazol-2-yl)-amine (Brimonidine) |

TABLE 1-continued

Representative α2 adrenergic receptor agonists

| Compound Formula | Compound Name |
| --- | --- |
| | (8-Bromo-quinoxalin-6-yl)-(4,5-dihydro-1H-imidazol-2-yl)-amine |
| | (8-Bromo-quinoxalin-5-yl)-(4,5-dihydro-1H-imidazol-2-yl)-amine |
| | (5-Bromo-3-methyl-quinoxalin-6-yl)-(4,5-dihydro-1H-imidazol-2-yl)-amine |
| | (5-Bromo-2-methoxy-quinoxalin-6-yl)-(4,5-dihydro-1H-imidazol-2-yl)-amine |
| | (4,5-dihydro-1H-imidazol-2-yl)-(8-methyl-quinoxalin-6-yl)-amine |
| | (4,5-dihydro-1H-imidazol-2-yl)-quinoxalin-5-yl-amine |
| | Tetrahydrozaline |
| | Naphazoline |

TABLE 1-continued

Representative α2 adrenergic receptor agonists

| Compound Formula | Compound Name |
|---|---|
| | Oxymetazoline |
| | Xylometazoline |
| | Epinephrine |
| | Norepinephrine |
| | Phenylephrine |
| | Methoxyamine |

The most preferred α2 adrenergic receptor agonist is brimonidine, (5-Bromo-quinoxalin-6-yl)-(4,5-dihydro-1H-imidazol-2-yl)-amine and pharmaceutically acceptable salts thereof, such as the tartrate salt.

In a preferred embodiment, the method of the present invention comprises topically administering to the skin of a subject a composition comprising a pharmaceutically acceptable carrier and a therapeutically effective amount of brimonidine.

One skilled in the art will recognize that the therapeutically effective amount of the α2 adrenergic receptor agonist to be used in the instant invention can vary with factors, such as the particular subject, e.g., age, diet, health, etc., severity and complications and types of the psoriasis sought to be treated or prevented, the formulation used, etc.

In view of the present disclosure, standard procedures can be performed to evaluate the effect of the administration of a topical composition to a subject, thus allowing a skilled artisan to determine the therapeutically effective amount of the α2 adrenergic receptor agonist. For example, the clinically observable beneficial effect of the topically administered α2 adrenergic receptor agonist can be observed or monitored directly from the subject, e.g., by measuring the psoriasis area severity index (PASI) before and after the treatment. PASI combines the assessment of the severity of lesions and the area affected into a single score in the range 0 (no disease) to 72 (maximal disease).

The clinically observable beneficial effect can be a situation that, when a composition of the present invention is administered to a subject after symptoms related to psoriasis are observable, the symptoms are prevented from further development or aggravation, or develop to a lesser degree than without administration of the specified composition according to embodiments of the present invention. The clinically observable beneficial effect can also be that, when a composition of the present invention is administered to a subject before symptoms related to psoriasis are observable, the symptoms are prevented from occurring or subsequently occur to a lesser degree than without administration of the composition of the present invention.

In one embodiment, a therapeutically effective amount of the α2 adrenergic receptor agonist will reduce a syndrome or a condition of discomfort of the subject associated with psoriasis or a symptom associated therewith by at least about 20%, for example, by at least about 30%, about 40%, about 50%, about 60%, about 70%, about 80%, about 90%, or about 100%.

In another embodiment, a therapeutically effective amount of the α2 adrenergic receptor agonist will prevent a syndrome or a condition of discomfort of the subject associated with psoriasis or a symptom associated therewith, or reduce the probability of its onset by at least about 20%, for example, by at least about 30%, about 40%, about 50%, about 60%, about 70%, about 80%, about 90%, or about 100%.

Dosages and dosing frequency will be determined by a trained medical professional depending on the activity of the compounds used, the characteristics of the particular topical formulation, and the identity and severity of the dermatologic disorder treated or prevented.

In an embodiment of the present invention, the topically administrable composition comprises 0.01% to 5% by weight of the α2 adrenergic receptor agonist. For example, the composition can comprise, 0.01%, 0.05%, 0.1%, 0.2%, 0.3%, 0.4%, 0.5%, 0.6%, 0.7%, 0.8%, 0.9%, 1%, 2%, 3%, 4% or 5%, by weight, of the α2 adrenergic receptor agonist.

In a preferred embodiment, the topically administrable composition comprises 0.05-0.5%, 0.07%-0.7% or 0.1-0.6% by weight of the α2 adrenergic receptor agonist.

To treat or prevent psoriasis or a symptom associated therewith, in view of the present disclosure, the topically administrable compositions of the invention can be topically applied directly to the affected area in any conventional manner known in the art, e.g., by dropper or applicator stick, as a mist via an aerosol applicator, via an intradermal or transdermal patch, or by simply spreading a formulation of the invention onto the affected area with fingers. Generally the amount of a topical formulation of the invention applied to the affected skin area ranges from about 0.1 g/cm$^2$ of skin surface area to about 5 g/cm$^2$, preferably, 0.2 g/cm$^2$ to about 0.5 g/cm$^2$ of skin surface area. Typically, one to four applications per day are recommended during the term of treatment.

Methods of the present invention can be used in conjunction with one or more other treatments and medications for psoriasis or a symptom associated therewith.

The other medicament or treatment can be administered to the subject simultaneously with, or in a sequence and within a time interval of, the administration of the α2 adrenergic receptor agonist, such that the active ingredients or agents can act together to treat or prevent psoriasis and symptoms associated therewith. For example, the other medicament or treatment and the α2 adrenergic receptor agonist can be administered in the same or separate formulations at the same or different times.

Any suitable route of administration can be employed to deliver the additional treatment or medication including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation.

In one embodiment, the α2 adrenergic receptor agonist according to embodiments of the invention is used in combination with a topical treatment with coal tar, dithranol (anthralin), corticosteroids like desoximetasone (Topicort), fluocinonide, vitamin D analogues (for example, calcipotriol), retinoids, Argan oil, etc.

In another embodiment, the α2 adrenergic receptor agonist according to embodiments of the invention is used in combination with phototherapy, such as daily, short, non-burning exposure to sunlight or with ultraviolet B (UVB) (315-280 nm).

In another embodiment, the α2 adrenergic receptor agonist according to embodiments of the invention is used in combination with photochemotherapy, i.e., the combined therapy of psoralen and ultraviolet A phototherapy (PUVA).

In yet another embodiment, the α2 adrenergic receptor agonist according to embodiments of the invention is used in combination with a systemic treatment, e.g., by injection or oral administration of medications, such as methotrexate, cyclosporine and retinoids (synthetic forms of vitamin A).

In yet another embodiment, the α2 adrenergic receptor agonist according to embodiments of the invention is used in combination with a biologic, such as Amevive®, Enbrel®, Humira®, and Remicade®.

Another aspect of the invention relates to a kit for treating or preventing psoriasis or a symptom associated therewith. The kit comprises:

(1) a topically administrable composition comprising a therapeutically effective amount of an $\alpha_2$ adrenergic receptor agonist and a pharmaceutically acceptable carrier; and (2) instructions for topically administering the topically administrable composition to a skin area of the subject for treating or preventing psoriasis or the symptom associated therewith, wherein the skin area is, or is prone to be, affected by psoriasis or the symptom associated therewith under the treatment or prevention.

In one embodiment of the invention, the topically administrable compositions is contained within one suitable container, such as a dropper, a jar, or a tube with a suitable small orifice size, such as an extended tip tube, made of any pharmaceutically suitable material. The topical formulations of the invention can be filled and packaged into a plastic squeeze bottle or tube. Suitable container-closure systems for packaging a topical formulations of the invention are commercially available for example, from Wheaton Plastic Products, 1101 Wheaton Avenue, Millville, N.J. 08332.

Preferably, instructions are packaged with the formulations of the invention, for example, a pamphlet or package label. The labeling instructions explain how to administer topical formulations of the invention, in an amount and for a period of time sufficient to treat or prevent psoriasis or a symptom associated therewith. Preferably, the label includes the dosage and administration instructions, the topical formulation's composition, the clinical pharmacology, drug resistance, pharmacokinetics, absorption, bioavailability, and contraindications.

A topically administrable composition that can be used in embodiments of the present invention comprising a pharmaceutically acceptable carrier and a therapeutically effective amount of an α2 adrenergic receptor agonist. The carriers useful for topical delivery of the specified compounds according to embodiments of the invention can be any carrier known in the art for topically administering pharmaceuticals, including, but not limited to, pharmaceutically acceptable solvents, such as a polyalcohol or water; emulsions (either oil-in-water or water-in-oil emulsions), such as creams or lotions; micro emulsions; gels; ointments; liposomes; powders; and aqueous solutions or suspensions. The pharmaceutically acceptable carrier includes necessary and inert pharmaceutical excipients, including, but not limited to, binders, suspending agents, lubricants, flavorants, preservatives, dyes, and coatings.

The topically administrable composition are prepared by mixing a pharmaceutically acceptable carrier with a therapeutically effective amount of an α2 adrenergic receptor agonist according to known methods in the art, for example, methods provided by standard reference texts such as, REMINGTON: THE SCIENCE AND PRACTICE OF PHARMACY 1577-1591, 1672-1673, 866-885 (Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

In one embodiment, the topically administrable composition is in the form of an emulsion. Emulsions, such as creams and lotions are suitable topical formulations for use in the invention. An emulsion is a dispersed system comprising at least two immiscible phases, one phase dispersed in the other as droplets ranging in diameter from 0.1 μm to 100 μm. An emulsifying agent is typically included to improve stability. When water is the dispersed phase and an oil is the dispersion medium, the emulsion is termed a water-in-oil emulsion. When an oil is dispersed as droplets throughout the aqueous phase as droplets, the emulsion is termed an oil-in-water emulsion. Emulsions, such as creams and lotions that can be used as topical carriers and their preparation are disclosed in REMINGTON: THE SCIENCE AND PRACTICE OF PHARMACY 282-291 (Alfonso R. Gennaro ed. 19th ed. 1995), hereby incorporated herein by reference.

In another embodiment, the topically administrable composition is in the form of a gel, for example, a two-phase gel or a single-phase gel. Gels are semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the invention are disclosed in REMINGTON: THE SCIENCE AND PRACTICE OF PHARMACY 1517-1518 (Alfonso R. Gennaro ed. 19th ed. 1995), hereby incorporated herein by reference. Other suitable gels for use with the invention are disclosed in U.S. Pat. No. 6,387,383 (issued May 14, 2002); U.S. Pat. No. 6,517,847 (issued Feb. 11, 2003); and U.S. Pat. No. 6,468,989 (issued Oct. 22, 2002), each of which patents is hereby incorporated herein by reference.

In an embodiment, the topically administrable composition comprises an aqueous gel comprising water and a water-gelling amount of a pharmaceutically acceptable gelling agent selected from the group consisting of carbomers, glycerine polyacrylate, and mixtures thereof, and the topical composition has a physiologically acceptable pH.

Polymer thickeners (gelling agents) that may be used in compositions according to embodiments of the present invention include those known to one skilled in the art, such as hydrophilic and hydroalcoholic gelling agents frequently used in the cosmetic and pharmaceutical industries. Preferably, the hydrophilic or hydroalcoholic gelling agent comprises "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STA-BILEZE®" (ISP Technologies, Wayne, N.J.). Preferably the gelling agent comprises between about 0.2% to about 4% by weight of the composition. More particularly, the preferred compositional weight percent range for "CARBOPOL®" is between about 0.5% to about 2%, while the preferred weight percent range for "NATROLSOL®" and "KLUCEL®" is between about 0.5% to about 4%. The preferred compositional weight percent range for both "HYPAN®" and "STA-BILEZE®" is between 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other preferred gelling polymers include hydroxyethylcellulose, cellulose gum, MVE/MA decadiene crosspolymer, PVM/MA copolymer, or a combination thereof.

In another preferred embodiment, the topically administrable composition is in the form of an ointment. Ointments are oleaginous semisolids that contain little if any water. Preferably, the ointment is hydrocarbon based, such as a wax, petrolatum, or gelled mineral oil. Suitable ointments for use in the invention are well known in the art and are disclosed in REMINGTON: THE SCIENCE AND PRACTICE OF PHARMACY 1585-1591 (Alfonso R. Gennaro ed. 19th ed. 1995), hereby incorporated herein by reference.

In an embodiment of the present invention, the topically administrable composition comprises at least one of a cream and an ointment comprising an agent selected from the group consisting of stearic acid, stearyl alcohol, cetyl alcohol, glycerin, water, and mixtures thereof, and the topical composition has a physiologically acceptable pH.

In another embodiment, the topically administrable composition is in the form of an aqueous solution or suspension, preferably, an aqueous solution. Suitable aqueous topical formulations for use in the invention include those disclosed in REMINGTON: THE SCIENCE AND PRACTICE OF PHARMACY 1563-1576 (Alfonso R. Gennaro ed. 19th ed. 1995), hereby incorporated herein by reference. Other suitable aqueous topical carrier systems include those disclosed in U.S. Pat. No. 5,424,078 (issued Jun. 13, 1995); U.S. Pat. No. 5,736,165 (issued Apr. 7, 1998); U.S. Pat. No. 6,194,415 (issued Feb. 27, 2001); U.S. Pat. No. 6,248,741 (issued Jun. 19, 2001); U.S. Pat. No. 6,465,464 (issued Oct. 15, 2002), all of which patents are hereby incorporated herein by reference.

The pH of the topical formulations of the invention are preferably within a physiologically acceptable pH, e.g., within the range of about 6 to about 8, more preferably, of about 6.3 to about 6.5. To stabilize the pH, preferably, an effective amount of a buffer is included. In one embodiment, the buffering agent is present in the aqueous topical formulation in an amount of from about 0.05 to about 1 weight percent of the formulation. Acids or bases can be used to adjust the pH as needed.

Tonicity-adjusting agents can be included in the aqueous topical formulations to be used in embodiments of the present invention. Examples of suitable tonicity-adjusting agents include, but are not limited to, sodium chloride, potassium chloride, mannitol, dextrose, glycerin, and propylene glycol. The amount of the tonicity agent can vary widely depending on the formulation's desired properties. In one embodiment, the tonicity-adjusting agent is present in the aqueous topical formulation in an amount of from about 0.5 to about 0.9 weight percent of the formulation.

Preferably, the aqueous topical formulations have a viscosity in the range of from about 15 cps to about 25 cps. The viscosity of aqueous solutions of the invention can be adjusted by adding viscosity adjusting agents, for example, but not limited to, polyvinyl alcohol, povidone, hydroxypropyl methyl cellulose, poloxamers, carboxymethyl cellulose, or hydroxyethyl cellulose.

In a preferred embodiment, the aqueous topical formulation is isotonic saline comprising a preservative, such as benzalkonium chloride or chlorine dioxide, a viscosity-adjusting agent, such as polyvinyl alcohol, and a buffer system such as sodium citrate and citric acid.

The topically administrable composition can comprise pharmaceutically acceptable excipients such as those listed in REMINGTON: THE SCIENCE AND PRACTICE OF PHARMACY 866-885 (Alfonso R. Gennaro ed. 19th ed. 1995; Ghosh, T. K.; et al. TRANSDERMAL AND TOPICAL DRUG DELIVERY SYSTEMS (1997), hereby incorporated herein by reference, including, but not limited to, protectives, adsorbents, demulcents, emollients, preservatives, antioxidants, moisturizers, buffering agents, solubilizing agents, skin-penetration agents, and surfactants.

Suitable protectives and adsorbents include, but are not limited to, dusting powders, zinc sterate, collodion, dimethicone, silicones, zinc carbonate, aloe vera gel and other aloe products, vitamin E oil, allatoin, glycerin, petrolatum, and zinc oxide.

Suitable demulcents include, but are not limited to, benzoin, hydroxypropyl cellulose, hydroxypropyl methylcellulose, and polyvinyl alcohol.

Suitable emollients include, but are not limited to, animal and vegetable fats and oils, myristyl alcohol, alum, and aluminum acetate.

In an embodiment of the present invention, the topically administrable composition further comprises one or more agent selected from the group consisting of a preservative, a local anesthetic and a skin humectant.

Suitable preservatives include, but are not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of parahydroxybenzoic acid; and other antimicrobial agents such as chlorhexidine, chlorocresol, benzoic acid and polymyxin.

Chlorine dioxide ($ClO_2$), preferably, stabilized chlorine dioxide, is a preferred preservative for use with topical formulations of the invention. The term "stabilized chlorine dioxide" is well known in the industry and by those skilled in the art. Stabilized chlorine dioxide includes one or more chlorine dioxide precursors such as one or more chlorine dioxide-containing complexes and/or one or more chlorite-containing components and/or one or more other entities capable of decomposing or being decomposed in an aqueous medium to form chlorine dioxide. U.S. Pat. No. 5,424,078 (issued Jun. 13, 1995), hereby incorporated herein by reference, discloses a form of stabilized chlorine dioxide and a method for producing same, which can be used as a preservative for aqueous ophthalmic solutions and is useful in topical formulations of the invention. The manufacture or production of certain stabilized chlorine dioxide products is described in U.S. Pat. No. 3,278,447, hereby incorporated herein by reference. A commercially available stabilized chlorine dioxide which can be utilized in the practice of the present invention is the proprietary stabilized chlorine dioxide of BioCide International, Inc. of Norman, Okla., sold under the trademark Purogene™ or Purite™. Other suitable stabilized chlorine dioxide products include that sold under the trademark DuraKlor by Rio Linda Chemical Company, Inc., and that sold under the trademark Antheium Dioxide by International Dioxide, Inc.

Suitable antioxidants include, but are not limited to, ascorbic acid and its esters, sodium bisulfite, butylated hydroxytoluene, butylated hydroxyanisole, tocopherols, and chelating agents like EDTA and citric acid.

Suitable moisturizers include, but are not limited to, glycerin, sorbitol, polyethylene glycols, urea, and propylene glycol.

Suitable buffering agents for use with the invention include, but are not limited to, acetate buffers, citrate buffers, phosphate buffers, lactic acid buffers, and borate buffers.

Suitable solubilizing agents include, but are not limited to, quaternary ammonium chlorides, cyclodextrins, benzyl benzoate, lecithin, and polysorbates.

Suitable skin-penetration agents include, but are not limited to, ethyl alcohol, isopropyl alcohol, octylphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate); and N-methylpyrrolidone.

In a preferred embodiment, a topically administrable composition according to embodiments of the invention further comprises titanium dioxide ($TiO_2$), preferably at an amount that is sufficient to mask the color of brimonidine or another colored ingredient in the formulation, but would not cause irritation to the skin. $TiO_2$ may cause mild irritation and reddening to the eyes, thus eye contact with the $TiO_2$—containing topically administrable composition should be avoided.

The topically administrable composition according to embodiments of the invention can include pharmaceuticals or their pharmaceutically acceptable salts, such as an α2 adrenergic receptor agonist, and optionally one or more other pharmaceutically active ingredients, including, but not limited to, coal tar, dithranol (anthralin), corticosteroids like desoximetasone (Topicort), fluocinonide, vitamin D analogues (for example, calcipotriol), retinoids, Argan oil, psoralen, methotrexate, cyclosporine, retinoids or other synthetic forms of vitamin A, Amevive®, Enbrel®, Humira®, and Remicade®.

The topically administrable composition according to embodiments of the invention can further include local anesthetics and analgesics, such as camphor, menthol, lidocaine, and dibucaine, and pramoxine; antifungals, such as ciclopirox, chloroxylenol, triacetin, sulconazole, nystatin, undecylenic acid, tolnaftate, miconizole, clotrimazole, oxiconazole, griseofulvin, econazole, ketoconazole, and amphotericin B; antibiotics and anti-infectives, such as mupirocin, erythromycin, clindamycin, gentamicin, polymyxin, bacitracin, and silver sulfadiazine; and antiseptics, such as iodine, povidine-iodine, benzalkonium chloride, benzoic acid, chlorhexidine, nitrofurazine, benzoyl peroxide, hydrogen peroxide, hexachlorophene, phenol, resorcinol, and cetylpyridinium chloride.

This invention will be better understood by reference to the non-limiting examples that follow, but those skilled in the art will readily appreciate that the examples are only illustrative of the invention as described more fully in the claims which follow thereafter.

Example 1

Gel Formulation

An exemplary gel formulation is prepared using methods known in the art, e.g., by mixing the following ingredients at the specified concentrations:

| Ingredient | Weight Percent |
| --- | --- |
| Brimonidine tartrate | 0.18% |
| Carbomer 934P | 1.25% |
| Methylparaben | 0.3% |
| Phenoxyethanol | 0.4% |
| Glycerin | 5.5% |
| 10% Titanium dioxide | 0.625% |
| Propylene glycol | 5.5% |
| 10% NaOH Solution | 6.5% |
| DI Water | QS |
| TOTAL | 100% |

Example 2

A discovery experiment was conducted using Alphagan®-P (0.15% brimonidine Tartrate) as a test solution for the treatment of psoriasis in a human subject.

The subject, a 52 year old woman, exhibited severe psoriasis on both elbows, across the back and parts of the leg. During an initial period of 30 days, she was not treated with any psoriasis medication and received skin treatment limited to soap and water only. Then, she received a 10 day treatment regiment with Alphagan®-P (0.15% Brimonidine Tartrate), by applying 1 ml Alphagan®-P twice per day to a skin area of psoriasis measuring approximately 3 inches by 6 inches on the left elbow. This application was done with a non-absorptive cotton swab in a manner that thoroughly wetted the area of psoriasis and then allowed to air dry. As a control, her right elbow continued to receive soap and water treatments only. The entire forty day protocol was repeated twice.

Two desirable effects were observed in the area of psoriasis that was treated with Alphagan®-P: (1) redness around the psoriasis plaque was dramatically reduced and (2) the sensation of itchiness was completely eliminated, although the size of the plaque was not significantly reduced. When the treatment was stopped the redness and itchiness returned. The results were reproducible upon repeated testing.

Results of this experiment demonstrate that topical application of an α2 adrenergic receptor agonist, such as brimonidine, to a skin area affected by psoriasis is effective to ameliorate symptoms of psoriasis, e.g., resulting in reduction of redness and the elimination of itchiness.

Without wishing to be bound by the theory, it is believed that an α2 adrenergic receptor agonist, such as brimonidine, may reduce blood flow to the skin area affected by psoriasis and slow down the rapid skin growth in the affected skin area, thereby resulting in treatment or prevention of psoriasis and its symptoms.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of treating psoriasis or a symptom associated therewith in a subject, the method comprising topically administering to a skin area of the subject a topical composition comprising a therapeutically effective amount of an α2 adrenergic receptor agonist and a pharmaceutically acceptable carrier, wherein the skin area is, or is prone to be, affected by psoriasis or the symptom associated therewith, and wherein the α2 adrenergic receptor agonist is brimonidine.

2. The method according to claim 1, wherein the composition comprises 0.01% to 5% by weight of the α2 adrenergic receptor agonist.

3. The method according to claim 2, wherein the composition is administered to the skin area at about 0.1 g/cm$^2$ to about 5 g/cm$^2$ of the skin area, one to four applications per day.

4. The method of claim 1, further comprising administering to the subject at least one additional treatment and medication for psoriasis or the symptom associated therewith.

5. The method of claim 1, wherein the topical composition further comprises titanium dioxide.

6. The method according to claim 1, wherein the topical composition is in a form selected from the group consisting of sprays, mists, aerosols, solutions, lotions, gels, creams, ointments, pastes, unguents, emulsions, and suspensions.

7. The method according to claim 1, wherein the topical composition comprises 0.05-0.5%, 0.07%-0.7% or 0.1-0.6% by weight of the α2 adrenergic receptor agonist.

8. The method according to claim 1, wherein the topical composition comprises an aqueous gel comprising water and a water-gelling amount of a pharmaceutically acceptable gelling agent selected from the group consisting of carbomers, glycerine polyacrylate, and mixtures thereof, and the topically administrable composition has a physiologically acceptable pH.

9. The method according to claim 1, wherein the topical composition comprises at least one of a cream and an ointment, each comprising an agent selected from the group consisting of stearic acid, stearyl alcohol, cetyl alcohol, glycerin, water, and mixtures thereof, and the topical composition has a physiologically acceptable pH.

10. The method according to claim 1, wherein the topical composition further comprises a preservative, a local anesthetic and a skin humectant.

\* \* \* \* \*